United States Patent [19]

Theeuwes

[11] Patent Number: 4,978,337
[45] Date of Patent: Dec. 18, 1990

[54] FORMULATION CHAMBER WITH EXTERIOR ELECTROTRANSPORT DELIVERY DEVICE

[75] Inventor: Felix Theeuwes, Los Altos, Calif.

[73] Assignee: Alza Corporation, Palo Alto, Calif.

[21] Appl. No.: 241,662

[22] Filed: Sep. 8, 1988

[51] Int. Cl.⁵ .................................................. A61M 5/14
[52] U.S. Cl. ...................................... 604/85; 604/251
[58] Field of Search ................. 604/85, 80, 81, 83, 604/84, 892.1, 251; 204/299, 308

[56] References Cited

U.S. PATENT DOCUMENTS

| | | |
|---|---|---|
| 3,677,268 | 7/1972 | Reeves . |
| 3,923,426 | 12/1975 | Theeuwes ............................ 417/48 |
| 3,991,755 | 11/1976 | Vernon et al. . |
| 4,540,403 | 9/1985 | Theeuwes ............................ 604/85 |
| 4,557,723 | 12/1985 | Sibalis ................................. 604/20 |
| 4,639,244 | 1/1987 | Rizk et al. ......................... 604/891.1 |
| 4,715,850 | 12/1987 | Tran .................................... 604/891 |

Primary Examiner—Stephen C. Pellegrino
Attorney, Agent, or Firm—Paul L. Sabatine; Edward L. Mandell; Steven F. Stone

[57] ABSTRACT

A drug delivery apparatus is disclosed comprising a formulation chamber and an electrotransport device on the outside of the formulation chamber for transporting an electrically charged drug from the outside into a medical fluid that flows through the formulation chamber over drug delivery time.

36 Claims, 4 Drawing Sheets

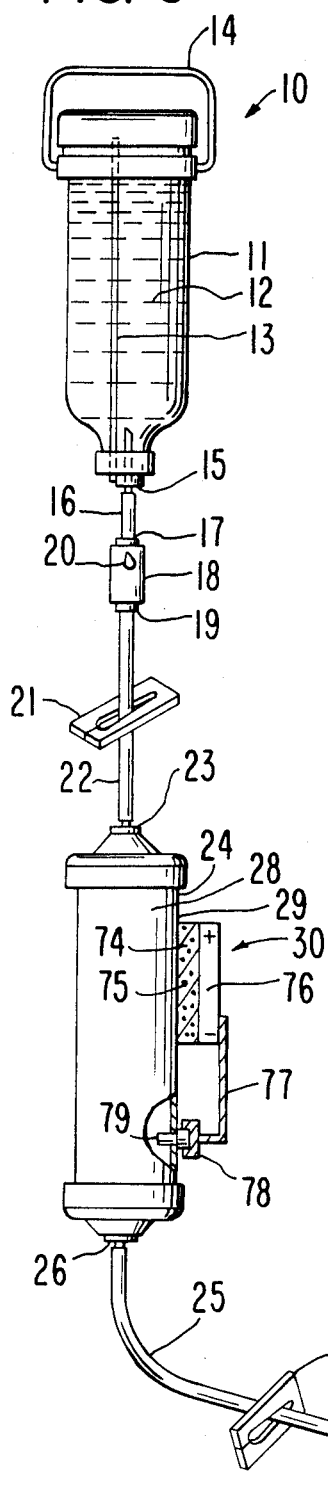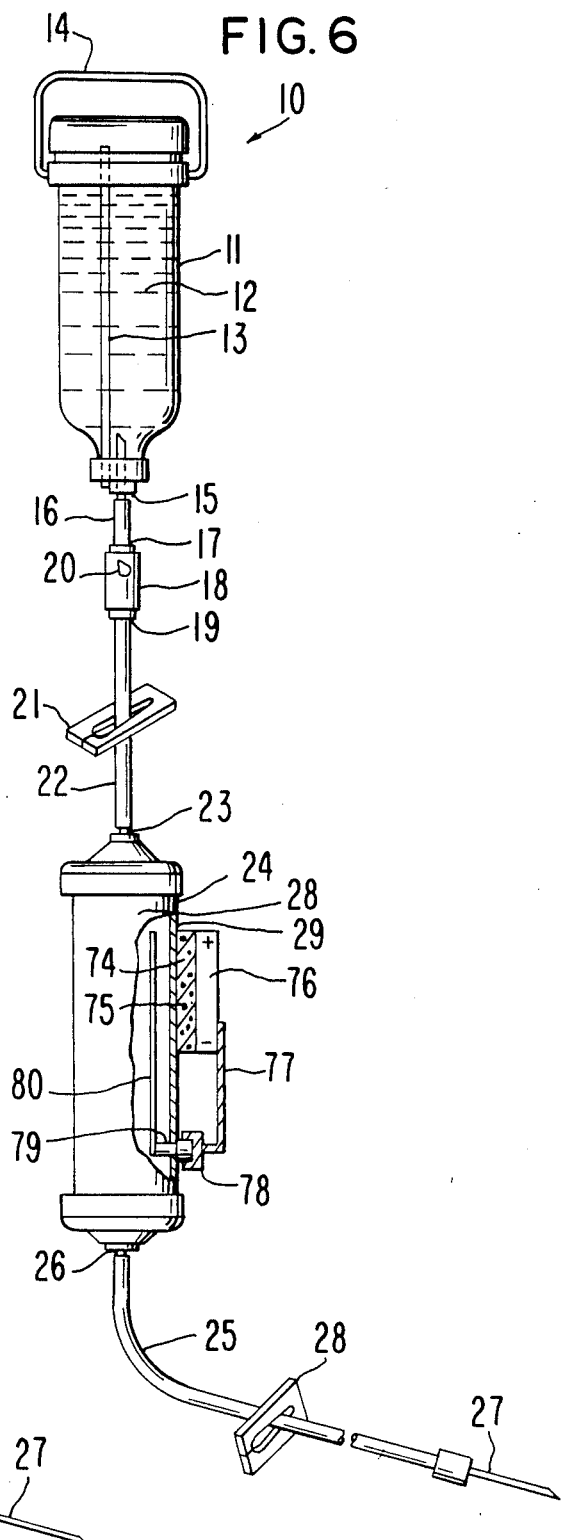
FIG. 5
FIG. 6

FORMULATION CHAMBER WITH EXTERIOR ELECTROTRANSPORT DELIVERY DEVICE

FIELD OF THE INVENTION

This invention pertains to a patient-care apparatus. The apparatus comprises, in combination, a chamber comprising an electrotransport device releasably positioned on the outside wall of the chamber for delivering a drug through its wall into the chamber. The invention also concerns an intravenous system comprising a container of a medical fluid, a chamber comprising an exterior electrotransport drug delivery device, and means for delivering a drug to a patient.

BACKGROUND OF THE INVENTION

The introduction of a drug into an intravenously, medically acceptable fluid is commonly done in clinical practice. Presently a beneficial drug is administered intravenously by one of the following procedures: (a) temporarily halting the flow of medical fluid and intravenously administering a solution of a drug to a patient through an injection port in an administration set, followed by resumption of administration of the medical fluid into the patients; (b) adding a drug to fluid inside a container, or into a volume control chamber in series with an administration set, which drug is carried by the flow of fluid into a patient; (c) introducing a drug into a piggyback container that is connected in tributary fashion to an administration set; or, (d) administering a drug by a pump that operates by one of various recognized pumping actions for producing flow, which flow of fluid containing a drug is pumped into a flow path, such as an indwelling catheter that enters the patient.

While these interior oriented techniques are used widely, they have certain disadvantages. For example, (e) the administration of a drug through repeated injections into an administration set is inconvenient and each time it is done it represents a break in sterility; (f) the use of pumps is expensive and inconvenient because of their size and weight; (g) the rate of drug delivery to a patient is dependent on internal fluid flow with all currently practiced means of drug infusion and, accordingly, it lacks drug delivery device control; (h) because of the relative chemical instability of medical solutions containing a drug, the administration of the drug often requires solubilization of the drug by the hospital pharmacists, or by the nurse at a time proximate to its administration; and (i) while it is current practice to give some drugs by brief infusions, typically of 30 to 120 minute duration repeated 3 or 4 times a day, it does not provide a means for carefully regulating the dose administered at any preselected time.

OBJECTS OF THE INVENTION

Accordingly, it is an immediate object of this invention to provide a patient-care apparatus that overcomes the shortcomings associated with the prior art.

Another object of this invention is to provide both a novel and a useful patient-care apparatus for introducing a drug into an intravenously acceptable fluid.

Another object of the invention is to provide a patient-care apparatus comprising an exterior member for introducing a drug into an intravenously acceptable fluid.

Another object of the invention is to provide a patient-care apparatus comprising a chamber and an exterior electro-transport device in contact with an outside surface of the chamber.

Another object of the invention is to provide a parenteral delivery system comprising a container of a medical fluid, a chamber, and an electrotransport device releasably placed on the outside of the chamber.

Another object of the invention is to provide a patient-care apparatus comprising a chamber and an exterior electrotransport device in contact with an outside surface of the formulation chamber for transporting a drug from an outside reservoir through the wall of the chamber to the inside of the chamber.

Another object of the invention is to provide a parenteral delivery system comprising (1) a primary fluid path and (2) a parallel fluid path comprising a formulation chamber comprising an exterior electrotransport drug delivery device in close contact with the exterior of a chamber for moving a drug through the wall of the chamber into a fluid flowing in the parallel path.

Another object of the invention is to provide a parenteral delivery system comprising (1) a primary path, and (2) a second path, and a chamber in communication with at least one path, and an electrotransport drug delivery device in contact with the outside of the chamber for transporting a drug from the outside through the wall of the formulation chamber to the inside of the formulation chamber.

Another object of this invention is to provide a parenteral delivery system comprising a means for administering a known amount of drug from an external drug-transporting means into a given volume of fluid as the fluid flows through a chamber.

Another object of the invention is to provide a parenteral delivery system that comprises an external drug delivery device that makes available a regimen of drug administration at intervals of drug administration at an electrically controlled specific rate, and for a specific duration, which can be alternated with intervals during which no drug is delivered from the exterior drug delivery means.

Another object of the invention is to provide a chamber comprising an exterior electrotransport device in drug delivery contact with the exterior of the chamber for programming drug therapy including means for adjusting the delivery to on, off, continuous, or a variable rate, consisting of low to high amounts of drug delivery over time.

Another object of the invention is to provide a parenteral system for delivering a drug intravenously by exterior electrotransport for controlled medical treatment.

Other objects, features and advantages of the present invention, it is believed, will be more apparent from the following detailed description of the disclosed embodiments, the drawings and the accompanying claims.

BRIEF DESCRIPTION OF THE DRAWINGS

In the drawings, which are not drawn to scale but are set forth to illustrate various embodiments provided by the invention, the drawing figures are as follows:

FIG. 5 is a view depicting a parenteral delivery system comprising a formulation chamber which is held onto the exterior surface by the formulation chamber by a snap-on connector; and, FIG. 6 is a view depicting a parenteral delivery system comprising a formulation chamber releasably held onto the exterior surface of the formulation chamber through a connecting arrangement that is attached to an internal grid.

In the specification and in the drawings, like parts in related drawings are identified by like numbers. The terms appearing earlier in the specification and in the description of the drawings are described hereafter in the disclosure.

MODES FOR CARRYING OUT THE INVENTION

Figure 1:
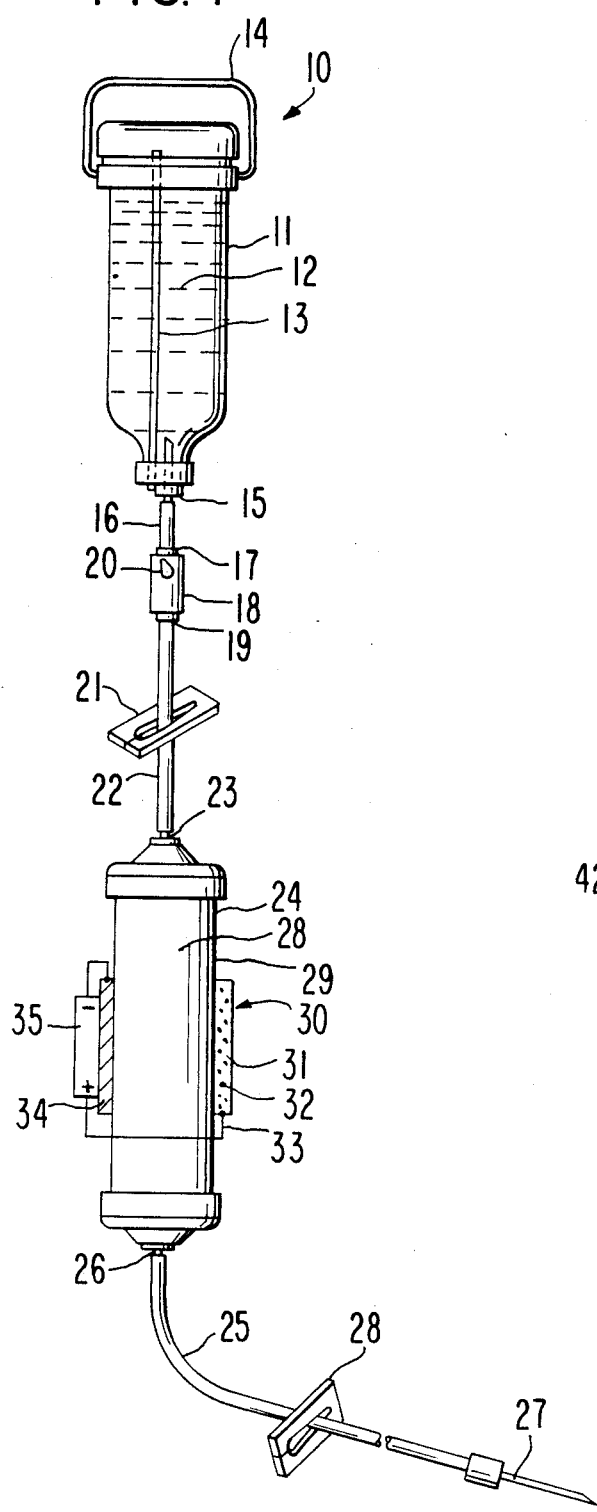
FIG. 1 is a perspective view showing an embodiment of the invention comprising a parenteral delivery system comprising a drip chamber and a formulation chamber with an exterior electrotransport drug delivery device.

FIG. 1 represents a parenteral delivery system 10 provided by this invention. Parenteral delivery system 10, as used herein, includes intravenous delivery. Parenteral delivery system 10 comprises a container 11 formed of glass or it is formed of a flexible or a semirigid, preferably transparent, plastic such as a high density polyolefin or a polyvinylchloride. Container 11 contains a medical fluid 12 adapted for parenteral, including intravenous, administration. Medical fluid 12 is typically a sterile solution, such as an aqueous solution of dextrose, a solution of dextrose in saline, saline, or an electrolyte solution. Medical fluid 12 also is a pharmaceutical vehicle or carrier for a beneficial agent that is to be administered to a recipient and as a carrier it is acceptable for intravenous administration. Container 11, in the embodiment illustrated, is a vented 13 container. Container 11, when manufactured of a flexible film, is nonvented, and in this manufacture a medical fluid in the container is at atmospheric pressure and the container collapses as it empties of a medical fluid. Container 11 usually is adapted to be hung neck down from a hanger 14. Container 11 at its end distant from its hanging end, that is at its neck end, comprises an administration port 15 adapted for receiving an administration set.

In one embodiment the administration set provided by this invention is used for (1) delivering medical fluid 12 from container 11 and, in a more preferred embodiment, it is used for (2) administering a beneficial agent introduced into medical fluid 12 by an electrotransport device. The administration set is sterile, pyrogen-free and, preferably, disposable. The administration set comprises the components described hereafter, and it connects with port 15 of container 11. Port 15 can be a diaphragm in container 11, not shown, or it can be a connector 16 that pierces the closed wall of container 11. Connector 16 is adapted to receive end 17 of a drip chamber 18, which end 17 snugly received connector 16. Drip chamber 18 has another end 19 that is an outlet end that established fluid communication between drip chamber 18 and the rest of the parenteral system 10. Drip chamber 18 is used to trap air and it permits the adjustment of the rate of fluid flow from container 11 as the flow proceeds dropwise 20. Drip chamber 18 comprises a wall that surrounds a lumen and the drip rate is governed by adjustable rolled clamp 21 on tube 22. Clamp 21 pinches the internal diameter of tube 22 for regulation flow in cooperation with drip sight chamber 18. Tube 22 connects to inlet end 23 of a formulation chamber 24. A tubing 25 is connected in fluid communication to outlet 26 of formulation chamber 24 and to an adapter needle assembly 27 that is inserted into a vein and sometimes an artery of a warm-blooded animal. Tube 25 passes through pinch clamp 28 that is a means for controlling fluid flow through tube 25 and, hence, into a patient.

Formulation chamber 24 is sized and adapted for use with parenteral delivery system 10. Formulation chamber 24 can comprise a cylindrical, rectangular, square, tubular shape, or any other shape designed for use with parenteral delivery system 10, that is amenable to low cost manufacturing. Formulation chamber 24 comprises a wall forming composition that surrounds an internal lumen 28, preferably comprising a light weight and a disposable composition. In one presently preferred embodiment the wall 29 is a window that permits charged drugs to pass through wall 29. Wall 29 in another manufacture is made in whole or in part of an ion exchange material, such as a cation exchange membrane, an anion exchange membrane, a microporous membrane, or a mosaic membrane. A typical cation exchange membrane is formed from a sulfonated cross-linked polystyrene such as poly(styrene trimethyl ammonium sulphate) cross-linked with divinyl benzene; sulphonic acid cation exchange polymers including phenol-sulphonic acid cation films, carboxylic sulphonic acid cation films, sulphonated polymerizates of polyvinyl aryl compounds; carboxylic cation exchange films such as copolymers of acrylic acid or methacrylic acid with divinyl aromatic compounds such as divinyl benzene, and the like.

Wall 29 of formulation chamber 24, when manufactured as an anion exchange membrane comprises anion exchange membranes wherein the active group is a member selected from quaternary ammonium, secondary amine, tertiary amines covalently bonded to an aromatic group and tertiary amines covalently bonded to an aliphatic group. The anion exchange materials include diethylaminocellulose, triethylaminocellulose, acetolaellulose (the reaction product of epichlorohydrin, triethanolamine and cellulose), quaternary ammonium derivatives of styrene polymers, and the like. Anion exchange membranes are available as Amberlite ®IRA-400; Dowex ®-1; Ionac ®A-550, and the like.

Wall 29 of formulation chamber 24, in another embodiment, can be formed of a porous material comprising glass, quartz, porous plastic, porous metal, or a ceramic. Generally the porous material comprises a pore size of submicron $\mu$ (micron) to about $10\mu$ and a porosity of about 10% to 70%. In another embodiment wall 29 of formulation chamber 24 comprises a cation film and an anion film, a cation film and a porous member, or an anion film and a porous member. The ion exchange polymers are known in *Encyclopedia of Polymer Science and Technology*, Vol. 7, pp 692-743 (1967), published by John Wiley & Sons, Inc.; in U.S. Pat. Nos. 2,990,332; 3,081,231; 3,143,465; 3,100,738; 3,313,686; 3,499,960 and 4,540,403.

In FIG. 1 an electrotransport drug delivery device 30, seen in opened section, is releasably positioned on the outside of wall 29, of formulation chamber 24. In a presently preferred embodiment, the electrotransport device is placed on the outside wall of formulation chamber 29. In another embodiment of the invention, electrotransport device 29 is placed on the outside surface of drip chamber 18. In this latter embodiment, drip chamber 18 comprises at least one surface that permits the passage of a charged drug, and the drip chamber is sized and adapted to receive an electrotransport device. In this instance, the drip chamber also serves as a formulation chamber. When the drip chamber carries on its outside surface an electrotransport apparatus, then the presence of a formulation chamber is optional, or an electrotransport apparatus can be optionally present on the outside of a drip chamber and on the outside of a formulation chamber.

Electrotransport device 30 can, in one embodiment, occupy a part of the outside surface of wall 29, or electrotransport device 30 can occupy the outside of wall 29 in its entirety. Electrotransport device 30 can be of any size and it is readily miniaturized, and thus it is capable of being used as a portable unit with a parenteral delivery system. Moreover, since electrotransport device 30 has no moving parts it may be turned on and off instantaneously and, therefore, it may be programmed to dispense a drug in an infinite variety of time delivery patterns The dispensing rate may be varied by varying the electrical input, by a microprocessor and, if desired, the electrotransport device is capable of being controlled remotely. The presence of a microporous optionally provides pattern drug administration.

Electrotransport device 30 is made for the ion transfer of a drug, as by migration of a drug ion through wall 29, which wall 29 permits the passage of a drug ion. The migration of a drug ion occurs when an electrical current is passed through a reservoir containing ionizable drugs. A drug in an ionic state in a reservoir is phoresed from the reservoir with a small current and electrically driven through wall 29 into a fluid in formulation chamber 24. Alternatively nonionized drug can be transported by electro-osmosis.

In FIG. 1 electrotransport device 30 comprises a reservoir 31 containing a drug 32. Reservoir 31 can be a fluid reservoir, a conductive gel layer, and the like. Electrotransport device 30 additionally comprises a pair of electrodes. The electrodes comprise anode electrode 33 that enters into reservoir 31 and a distant cathode electrode 34 that is in direct contact with outside wall 29. Anode 33 is connected to the positive pole of an electrical power source 35, and cathode 34 is connected to the negative pole of the same electrical power source 35. Typically a battery can be used as a direct current power source. An optional variable rheostat can be placed on the cathode path for regulating the flow electrons.

Anode electrode 33 and cathode electrode 34 can be made from conventional materials. Typical materials used for making electrodes include silver, platinum, copper, and the like. In a presently preferred embodiment the electrodes are selected from materials that do not produce an appreciable amount of unwanted gas and allow such unwanted gas to escape into the environment. A presently preferred electrode comprises a silver-silver chloride electrode. An optional vent, of the type of air vents known to the prior art, can be manufactured into the reservoir for the venting gas.

Electrotransport device 30 delivers drug 32 from reservoir 30 by electrodialysis or by electro-osmosis. Electrotransport device 30 operates to deliver drug 32 by electrodialysis when wall 29 is formed of an ion exchange material, such as a cation exchange membrane, and a drug 32 that exhibits the ability to ionize, such as salbutamol hydrochloride. The drug is delivered in this operation when a voltage difference is applied across cathode 34 and anode 33 through a cation exchange wall 29 interposed between the electrodes. When the voltage difference is applied drug will flow through cation exchange wall 29 into the lumen 28 of formulation chamber 24. The drug will enter medical fluid 12 for administration to a patient. Electrotransport device 30 operates to deliver drug 32 by electro-osmosis when wall 29 is formed of a porous material and when a drug 32, such as hydrocortisone, is essentially neutral in an electrical field. In electro-osmosis wall 29 acts as a stationary, solid, porous body through which wall 29 drug 32 passes from reservoir 31. By applying a potential difference to the electrotransport device fluid in reservoir 31 will move through porous wall 29 simultaneously transporting the neutral drug 32 through a porous wall 29 into a medical fluid 12 flowing through formulation chamber 24.

In another embodiment provided by the invention, electrotransport device 30 is used for ion migration of drug 32 when wall 29 is formed of an anion exchange film. In this embodiment electrotransport device 30 delivers drug 32 by establishing a voltage difference across cathode 34 that now enters reservoir 31 and an anode 33 in contact with a distant surface of wall 29. In this operation drug 32, such as sodium indomethacin, useful as an anti-inflammatory, antipyretic or analgesic therapeutic, in fluid in reservoir 31, such as an aqueous fluid, in an electrical field will ionize and form a mobile drug with a negative charge that moves through anion exchange wall 29. That is, drug 32 will be electrically transported through anion exchange wall 29 into formulation chamber 24, wherein it is added to medical fluid 12 flowing through formulation chamber 24.

Figure 2:
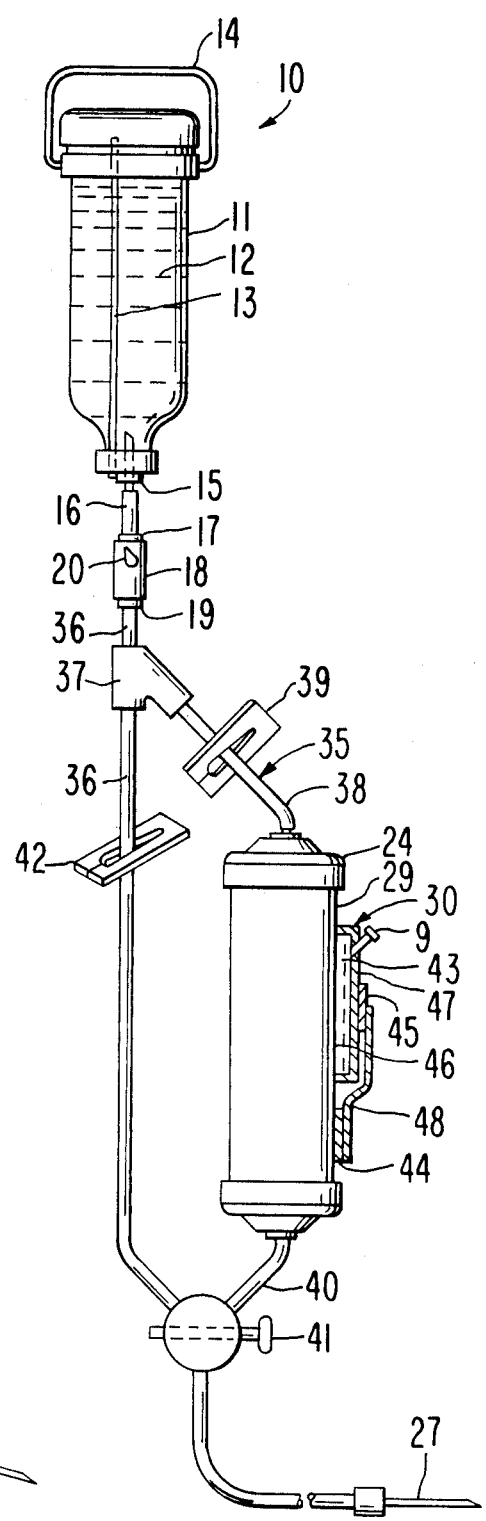
FIG. 2 is a perspective view depicting an embodiment of the invention comprising a parenteral delivery system comprising a side arrangement comprising a formulation chamber and an electrotransport drug delivery device in contact with the exterior of the formulation chamber.

FIG. 2 illustrates another embodiment provided by the invention. In FIG. 2 there is illustrated parenteral delivery system 10 comprising container 11, medical fluid 12, vent 13, hook 14, administration port 15, connector 16, adapter 17, drip chamber 18 and exit member 19. Intravenous delivery system 10 comprises a side arrangement or parallel path 35 connected to primary path 36 at branch couple 37. Branch couple 37 can be made as a Y-type connecting tube for receiving primary path 36 and side path 35. This provides medical fluid 12 to primary path 36 and parallel path 35. Parallel path 35 is connected through tube 38 to formulation chamber 24. A clamp 39 is provided on tube 38 for regulating fluid flow through formulation chamber 24. Formulation chamber 24 connects to tube 40 for conveying medical fluid 12 to valve 41. Valve 41 can receive medical fluid 12 from primary path 36 that passes through clamp 42. Valve 41 can be positioned to receive medical fluid 12 from primary path 36, or from parallel path 35, or from both primary path 36 and parallel path 35, that is administered to a patient through injection port 27.

Formulation chamber 24 comprises a releasably positioned electrotransport device 30 on its outside wall 29. Electrotransport device 30 comprises a first electrode 43, a second electrode 44, and a battery 45. First electrode 43 also serves in operation as a reservoir 46. In this manufacture the electrode-reservoir is formed of at least one of a conductive gel layer, a fluid, a suspension, a colloid, or the like, wherein the electrode-reservoir is in any physical-chemical form capable of containing an ionic agent. The electrode-reservoir combination is in contact with a current distribution conductive member or layer 47, which is laminated in laminar arrangement to one side of the electrode-reservoir combination. Current distribution conductive layer 47 is formed of aluminum foil, copper foil, or the like. Second electrode 44 is composed of a conductive gel and it carries, in laminar arrangement, a current distribution conductive member, illustrated as layer 48. Battery 45 is arranged with one of its poles, for example the negative pole, in contact with current distribution conductive layer 47 of first electrode 43. The positive pole of battery 45 contacts current distribution conductive layer 48 of second electrode 44. Electrotransport apparatus 30 is further equipped with an injection port 9 for adding, or recharging drug into reservoir electrode combination 43. Electrotransport device 30 also is provided with an insulating backing layer or housing member, not seen in FIG. 2.

Figure 3:
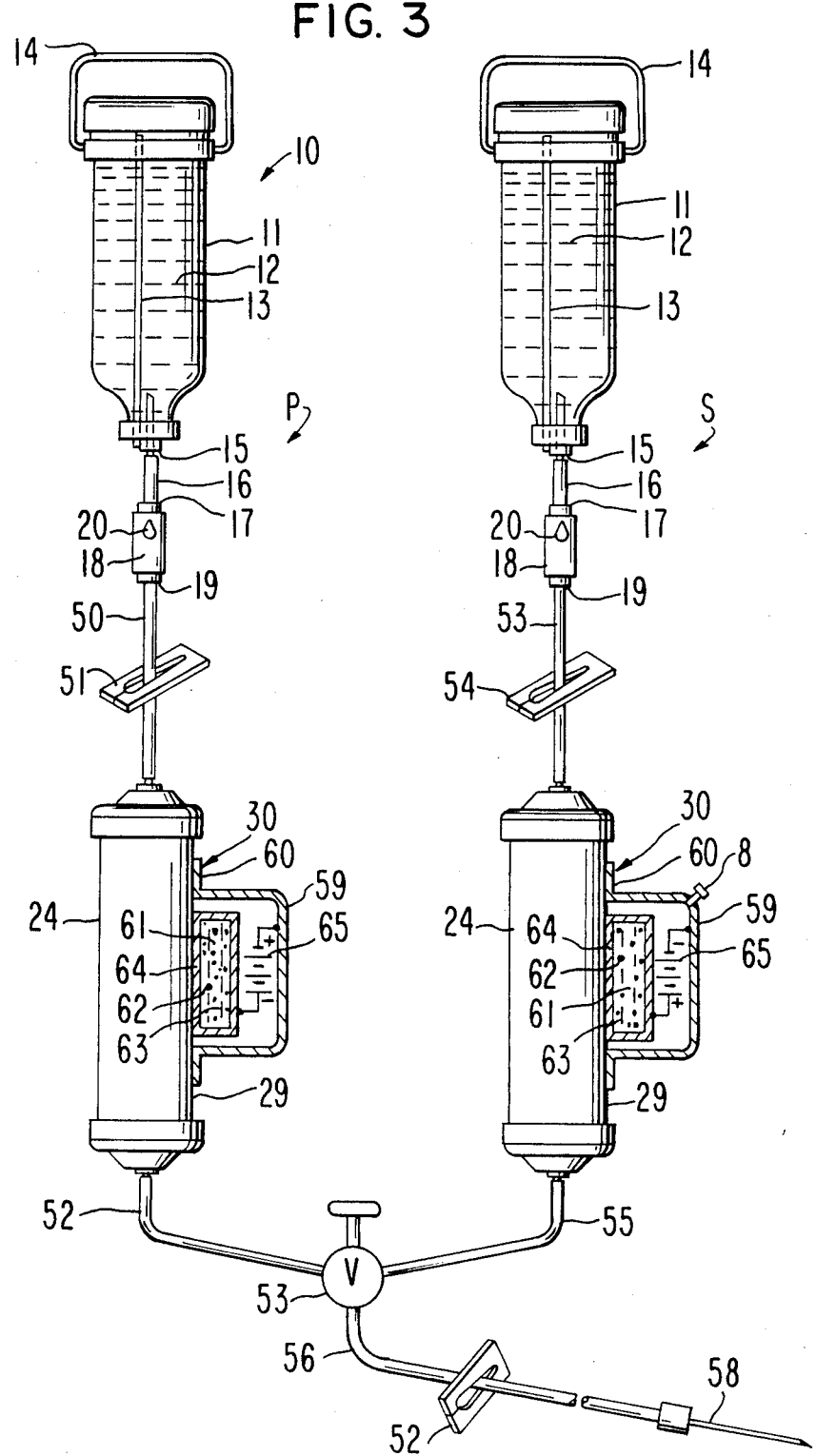
FIG. 3 is a view illustrative a parenteral delivery system comprising a primary deliver path, and a secondary delivery path, with a drip chamber in each path and formulation in each path and an electrotransport in exterior, releasably held contact with the formulation chamber.

FIG. 3 illustrates another embodiment provided by the invention. In FIG. 3 there is illustrated a parenteral delivery system 10 comprising a primary path P and a secondary path S. The primary path comprises a container 11, a medical fluid 12 in container 11, an internal vent 13, a hook 14, administration connecting port 15, connector 16, adapter 17, drip chamber 18, drip chamber exit port 19, and drop 20. The primary path comprises tube 50 that passes through flow regulator clamp 51, used for the adjustment of the rate of flow of medical fluid 12 from container 11 as the flow proceeds dropwise. Drip chamber 18 is used for regulating the drop 20 rate for the administration of solutions, such as glucose, saline and the like intravenous solutions, a drop at a time. The primary path enters formulation chamber 24 connected to exit tube 52 for conveying medical fluid 12 to valve 53. The secondary fluid path comprises a container 11, a medical fluid 12 in container 11 that is the same or a different medical fluid 12 than in the primary fluid path, internal vent 13, hook 14, administration couple port 15, connector 16, adapter 17, drip chamber 18, drip chamber exit port 19 and drop 20. The secondary path 53 passes through roller flow clamp 54 and into formulation chamber 24. The secondary formulation chamber 24 connects to exit tube 55, for conveying medicine 12 to valve 53. Valve 53 can be regulated for receiving fluid from the primary path, from the secondary path, or from both paths. In either operation medical fluid exits through valve 53, hence through tube 56 that passes through clamp 57 to patient injector member 58.

In the primary path an electrotransport device 30 is releasably positioned on the outside wall 29 of formulation chamber 24. The electrotransport device 30 can have any shape, for example, square, rectangular, oval, circular, or the like, for placement on synthetic wall surface 29. In FIG. 3 electrotransport device 30 is seen in opened section and it comprises an outer housing 59 that extends down to formulation chamber 24 ending in a lip 60 that extends along the outside surface of wall 29. Electrotransport device 30 comprises a wall 64 that surrounds and defines a reservoir 61 containing a drug 62. Drug 62 can be mixed with a vehicle 63, such as a solution, gel or the like. Electrotransport wall 64 can be formed of a microporous, a semipermeable composition, or the like, and wall 64 is sufficiently dense to avoid leakage of drug, or of solution, when not in operation, but wall 64 is porous to permit migration of charged drug 62 under the influence of an imposed electrical field.

An electrical source such as a battery 65 is positioned between reservoir 61 and the inside of housing 59. Battery 65 comprises a cell or a group of cells connected in series to provide the voltage required to migrate drug 62 from reservoir 61. The orientation of battery 65 is determined by the charge of drug 62. When a drug 62 is negatively charged in solution, suspension, gel or the like, then the negative pole of battery 65 connects to reservoir 61 and the positive pole of battery 65 connects to housing 59, as seen in the primary path. When drug 62 is positively charged in solution, suspension, gel or the like, the positive pole of battery 65 connects to reservoir 61, and the negative pole of battery 65 connects to housing 59 as seen in the secondary path. In one embodiment battery 65 can be any miniaturized battery cell arranged and connected in series to obtain the desired operating voltage. The battery can comprise flexible sheets of conductive polymers with high surface area relative to thickness to provide adequate current densities. Electrotransport apparatus 30 can be equipped with a gas vent 8 for letting gas escape from the electrotransport apparatus. Gas vent 8 can be a hydrophobic membrane filter which is permeable to air, but not to liquid. The hydrophobic filters can comprise polyflurotetraethylene, hexafluropropylene tetrafluroethylene copolymer, and the like.

Housing 59 comprises a flexible conductive polymeric composition, such as a polyolefin, a vinyl polymer, a polyamide, and the like, preferably impregnated with carbon, copper, or the like. In another embodiment housing 59 comprises a polymer coated on one surface with copper, or the like. The inside coated surface of housing 59 contacts the outside surface of wall 29 of formulation chamber 24. Electrotransport device 30 is releasably, or permanently, held by lip 60 onto wall 29 by any means for holding and making electrical contact. The means include ionically or electrically conductive adhesives coated onto the underside of lip 60, or onto the outside of wall 29 of formulation chamber 24. The adhesive can be of natural or synthetic origin, such as phenolic, styrene-butadiene, acrylate, silicone polymer, epoxy adhesives having dispersed therein conductive particles such as carbon, or copper particles, and the like; and, in addition, ion conductive particles such as ion exchange beads, hydrophilic crosslinked polymers, and the like.

Figure 4:
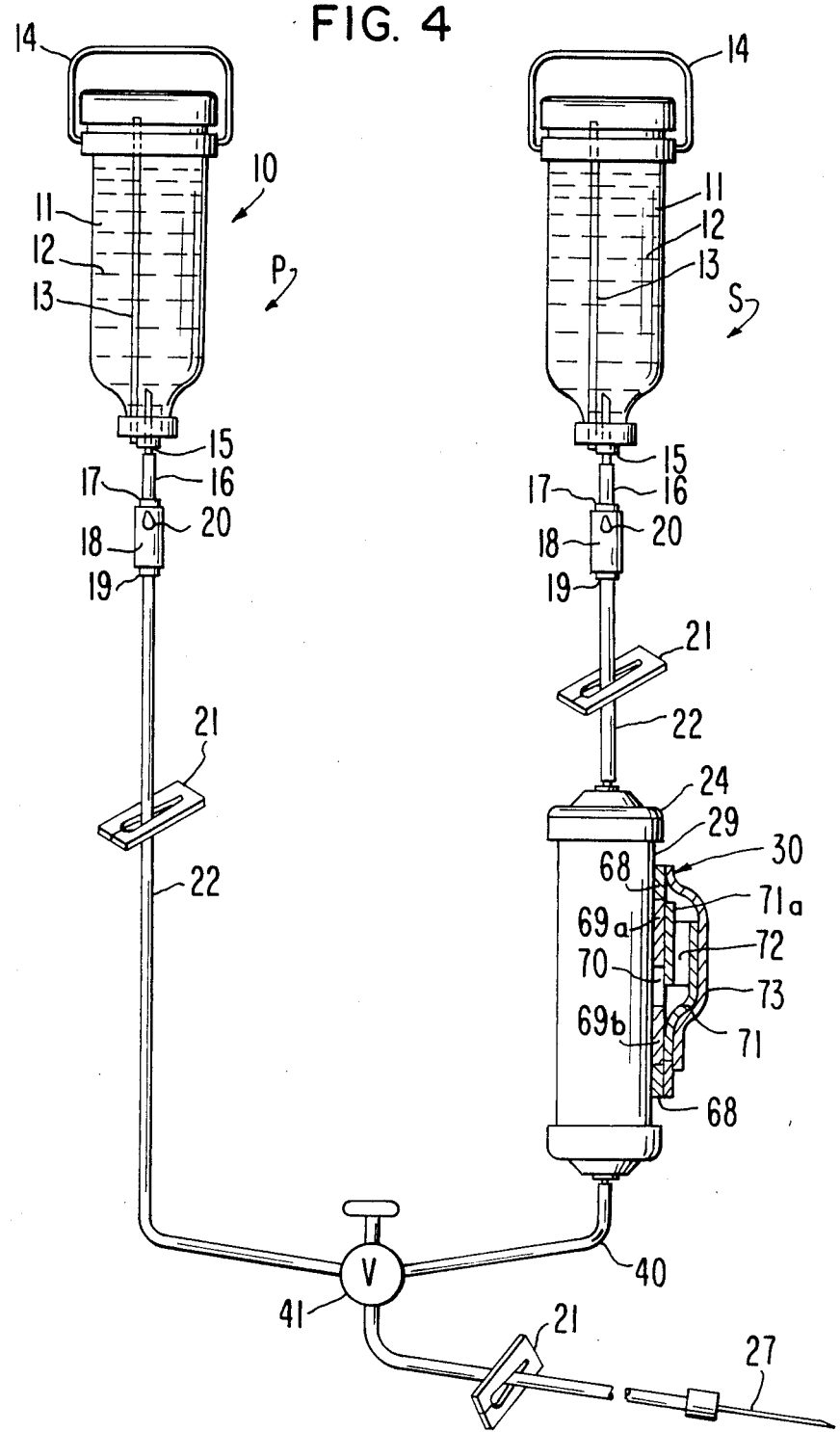
FIG. 4 is a view depicting a parenteral delivery system comprising a primary fluid path and a secondary fluid path, which secondary path comprises a formulation chamber comprising an electrotransport device in contact with the exterior surface of the formulation chamber.

FIG. 4 illustrates an intravenous delivery system 10 comprising a primary fluid path P and a secondary fluid path S. The primary path is used to deliver medical fluid 12, essentially free of a medicament, directly to a patient. The primary path is sterile and pyrogen-free. The primary path comprises the components described in FIGS. 1 to 3. The secondary path comprises a container 11 of medical fluid, which container is of identical or smaller volume than the container in the primary path. The medical fluid 12 in the secondary path is a pharmaceutical vehicle for intravenous administration, that is, it is a pharmaceutical carrier for a drug that is to be administered to a recipient. The secondary path is sterile and pyrogen-free. The secondary path comprises the components previously described in FIGS. 1 to 3.

The secondary fluid path S provided by the invention is used to deliver medical fluid 12 to which a drug is added by electrotransport device 30. Electrotransport device 30 comprises a housing 73 that encloses a pair of electric pads 69a and 69b separated by a space 70. Housing 73 also encloses a power source or battery 72, which battery is connected through a pair of electrodes 71a to electric pad 69a and electrode 71b to electric pad 69b for establishing an electric flow path. In operation an electric current is passed through an electric pad containing an ionized drug, which ionized drug, under the influence of the electrical current, migrates from the pad. The ionized drug then passes through the wall of the formulation chamber and on into medical fluid flowing through the formulation chamber. The electrical potential affects ionized drugs at the electrotransport device formulation chamber interface and drives the drug through the ion exchange, or the pores of the wall of the formulation chamber. Positive drug ions can be passed into the formulation chamber from a positive pad, while drug ions of negative charge can be passed into the formulation chamber from a negative pad.

Medical fluid 12 in reservoir container 11 is typically a sterile solution, such as dextrose, a solution of an electrolyte, or saline. Medical fluid 12 also is a pharmaceutical vehicle, or a pharmaceutically acceptable carrier for a drug that is to be administered to a recipient through a delivery member. The initial volume of medical fluid in a container will be a volume sufficient for performing a preselected therapeutic program. Container 11 can be a small volume container, or container 11 can be a large volume container. Container 11, as presently used herein, generally will have a small volume capacity of about 100 cc to 350 cc, and a large volume container will have a capacity of 250 cc to 1000 cc. Containers of other capacities likewise can be used for the present purpose.

The beneficial drug present in the electrotransport apparatus can be in any pharmaceutical state that lends itself to forming a charge bearing drug. The pharmaceutically acceptable forms that can initially be charged into the electrotransport device include liquid and solid forms. The solid forms comprise crystalline, microcrystalline, particle, pellet, granule, powder, dry, spray-dried, lyophilized, and like forms that form a charged, ionized drug. Gel and semi-solid forms optionally can be used for the present purpose. The drugs used in various disease conditions for therapy by electrotransport include dexamethasone sodium phosphate for musculoskeletal inflammatory conditions, insulin for diabetes, vidarabine monophosphate for keratitis herpes virus, vasopressin for lateral septal neuron activity, penicillin for pneumonia and abscesses of the lungs, and the like. The system also is very useful for delivering polypeptides and large protein molecules. The electrotransport device generally contains an amount of beneficial drug for executing a prescribed therapeutic program, usually from 10 nanograms to 5 grams, or more of drug.

FIG. 5 illustrates a delivery system 10 comprising a container 11 containing a medical fluid 12. Container 11 connects through a tube 22 to a formulation chamber 24. Formulation chamber 24 surrounds an internal lumen 28, and formulation chamber 24 comprises an electrotransport device 30 positioned on the outside wall surface 29 of formulation chamber 24. Electrotransport device 30 comprises a reservoir 74 containing a drug 75, which reservoir 74 is in contact with outer wall surface 29. Reservoir 74 is in contact with a battery 76, with one pole of battery 76 connected through a lead 77 to a connector 78. Connector 78 is adapted to releasably connect to an electrode 79, which electrode 79 extends through wall 29 of formulation chamber 24. Connector 78 provides a means for replacing electrotransport device 30 that contains the same or different drug 75. FIG. 6 illustrating the added embodiment of electrode 79 connected to an internal grid 80. Internal grid 80 is a counter electrode, that is, it functions as a return electrode closing the circuit. Typical materials comprising grid 80 include silver, platinum, silver chloride zinc alloy, silver platinum alloy, copper silver alloy, silver silver, and the like.

This novel and useful invention provides an apparatus and method for the obtainment of precise control of drug delivery into a parenteral delivery system for administration to a warm-blooded animal. While there has been described and pointed out features of the invention as applied to presently preferred embodiments, those skilled in the art will appreciate that various modifications, changes, additions, and omissions in the invention illustrated and described can be made without departing from the spirit of the invention.

I claim:

1. In a drug delivery apparatus comprising a fluid reservoir and means connected thereto for conveying a beneficial drug to a recipient, the improvement in the drug delivery apparatus, comprising:
   (a) a formulation chamber comprising:
      (1) an inlet connected to said conveying means for letting fluid into the chamber;
      (2) an outlet connected to said conveying means for letting fluid leave the chamber;
      (3) a wall that surrounds the chamber, with the improvement comprising means in the wall for letting an ionized drug pass through the wall; and
   (b) an electrotransport device positioned on the outside of the wall for providing a drug to the means for letting drug pass through the wall, the electrotransport device comprising:
      (4) a housing that surrounds an internal space;
      (5) a pair of electrodes in spaced relation disposed within the device; and,
      (6) a beneficial drug in the device initially present between the electrodes.

2. The drug delivery apparatus according to claim 1, wherein the means in the wall of the formulation chamber comprises an anion exchange composition.

3. The drug delivery apparatus according to claim 1, wherein the means in the wall of the formulation chamber comprises a cation exchange composition.

4. The drug delivery apparatus according to claim 1, wherein the means in the wall of the formulation chamber comprises a microporous composition.

5. The drug delivery apparatus according to claim 1, wherein the electrodes are connected to an electrical power source.

6. The drug delivery apparatus according to claim 1, wherein the formulation chamber is a drip chamber.

7. The drug delivery apparatus according to claim 1, wherein the drug is a peptide.

8. The drug delivery apparatus according to claim 2, wherein the electrodes are connected to a power supply comprising a microprocessor.

9. The drug delivery apparatus according to claim 2, wherein the electrodes are connected to a power supply comprising a microprocessor for patterning drug administration.

10. The parenteral delivery system for administering a beneficial drug to a recipient according to claim 12, wherein one of the electrodes is in the primary pat.

11. An improvement in a parenteral delivery system for administering a therapeutic drug to a recipient, the delivery system comprising:
(a) a reservoir comprising a pharmaceutical fluid;
(b) a formulation chamber in fluid communication with the reservoir, and wherein the improvement comprises in said formulation chamber a wall at least in part iontophoretically permeable to the passage of a drug;
(c) an electrotransport device positioned on the outside surface of the formulation chamber for transporting a drug through said wall into the formulation chamber, the electrotransport device comprising:
(1) a housing that surrounds an internal space;
(2) a drug reservoir comprising a therapeutic drug; and,
(3) a pair of electrodes in spaced relation in the device for providing an electric current for migrating a drug from the drug reservoir and into the formulation chamber; and
(d) means in communication with the formulation chamber for conveying the therapeutic drug from the delivery system to a patient in need of therapy.

12. The parenteral delivery system according to claim 11, wherein the electrodes are connected to an electrical power source.

13. The parenteral delivery system according to claim 11, wherein the wall composition comprises a member selected from the group consisting of anionic, cationic and microporous compositions.

14. The parenteral delivery system according to claim 11, wherein the formulation chamber is a drip chamber.

15. The parenteral delivery system according to claim 11, wherein the electrotransport device comprises an air vent.

16. A parenteral delivery system for administering a beneficial drug to a recipient, wherein the parenteral system comprises:
(a) a primary path, said primary path comprising:
(1) a reservoir comprising a medical fluid;
(2) a drip chamber in fluid communication with the reservoir and comprising means for conveying the medical fluid to the recipient; and
(b) a by-pass that circumvents the primary path and comprises means for connecting thereto, said by-pass comprising:
(1) a formulation chamber comprising at least in part a wall iontophoretically permeable to the passage of a drug; and
(2) an electrotransport device positioned on the outside of the formulation chamber, said electrotransport device comprising:
(i) a housing comprising a wall that surrounds an internal space;
(ii) a drug reservoir comprising an ionizable drug; and,
(iii) a pair of electrodes for providing an electrical current for migration of an ionized drug from the electrotransport drug reservoir through the iontophoretically permeable wall into the parenteral delivery system; and,
(c) means for conveying the beneficial drug from the formulation chamber to the recipient.

17. The parenteral delivery system for administering the beneficial drug according to claim 16, wherein the electrotransport device comprises an air vent.

18. A drug delivery apparatus, comprising:
(a) a formulation chamber comprising:
(1) a wall that surrounds an internal space, said wall comprising at least in part compositional means for letting an ionic drug pass through the wall;
(2) an inlet for letting fluid into the chamber;
(3) an outlet for letting fluid leave the chamber; and,
(b) an electrotransport device positioned on the outside of the wall and in contact with the compositional means for letting an ionic drug pass through the wall, said electrotransport device comprising:
(4) a backing layer comprising a non-conductive composition;
(5) a first electrode and second electrode in spaced apart orientation in the electrotransport device, said electrodes comprising a current conductive layer and a gel layer; and,
(6) a battery in the electrotransport device for providing electrical current to the electrode; and,
(c) means for delivering the drug from the outlet to a recipient in need of said drug.

19. The drug delivery apparatus according to claim 18, wherein the current conductive layer of the electrode comprises a side in contact with the inside of the backing layer.

20. The drug delivery apparatus according to claim 18, wherein the gel layer comprises a side in contact with the current conductive layer of the electrode.

21. The drug delivery apparatus according to claim 18, wherein the battery is between the electrodes and in electrical communication therewith.

22. The drug delivery apparatus according to claim 18, wherein the current conductive layer of the electrode comprises a member selected from metallic and aluminum compositions.

23. The drug delivery apparatus according to claim 18, wherein an adhesive holds the electrotransport device on the outside of the formulation chamber.

24. The drug delivery apparatus according to claim 18, wherein an adhesive releasably holds the current conductive layer and the gel layer in laminated arrangement.

25. The drug delivery apparatus according to claim 18, wherein an ionic drug is in the gel.

26. The drug delivery apparatus according to claim 18, wherein a drug that forms a charged drug in an electrical current is in the gel.

27. A drug delivery apparatus comprising, in combination:
(a) a formulation chamber comprising:
(1) a wall that surrounds an internal space, said wall comprising compositional means for letting a charged drug migrate through the wall into the formulation chamber;
(2) an inlet for letting fluid enter the chamber;
(3) an outlet for letting fluid leave the chamber; and, (b) a drug electrotransport device in contact with the exterior wall of the formulation chamber, said electrotransport device comprising:

(4) housing means for covering an internal area, said housing means comprising a composition conducive for the flow of an electrical current and lip forming a periphery for mounting the electrotransport device on the exterior wall;

(5) a reservoir in the area, said reservoir comprising a drug;

(6) a battery in the area, said battery in electrical communication with the reservoir and with the housing to define a complete electrical circuit, whereby drug in an electric circuit migrates from the reservoir and through the wall into the formulation chamber.

28. The drug delivery device according to claim 27, wherein an adhesive comprising an electrically conductive composition is coated onto the lip for holding the electrotransport device on the exterior wall.

29. The drug delivery device according to claim 27, wherein the reservoir is electrically insulated from the housing means.

30. The drug delivery device according to claim 27 wherein the electrotransport device comprises an air vent.

31. The drug delivery device according to claim 27 wherein the electrotransport device comprises a port for admitting a drug into the electrotransport device.

32. The drug delivery apparatus according to claim 27, wherein one of the electrodes is in the formulation chamber.

33. The drug delivery apparatus according to claim 27, wherein a drug in the apparatus is a polypeptide.

34. A drug delivery apparatus, comprising:
(a) a formulation chamber comprising:
  (1) a wall that surrounds and internal chamber;
  (2) means in the wall for letting an ionized drug pass through the wall;
  (3) an inlet for letting fluid enter the chamber;
  (4) an outlet for letting fluid exit the chamber;
  (5) means connected to the outlet for conveying fluid from the chamber to a recipient;
(b) an electrotransport device positioned on the outside of the wall for providing a drug to the means for letting ionized drug pass through the wall, the electrotransport device comprising:
  (6) a source of electrical power;
  (7) a pair of electrodes, connectable to the power source, and in spaced relation disposed on the outside of the wall; and,
  (8) a beneficial drug in the electrotransport device and adapted to be iontophoretically delivered through the wall by at least one of the electrodes.

35. A parenteral delivery system for administering an intravenously acceptable drug to a recipient, the delivery system comprising:
(a) a reservoir of an intravenously acceptable fluid;
(b) a formulation chamber in fluid communication with the fluid reservoir, the formulation chamber comprising wall means for permitting an iontophoretically delivered drug to pass therethrough;
(c) means in contact with the formulation chamber for conveying fluid to a recipient;
(d) an electrotransport device positioned on the outside of the formulation chamber for iontophoretically transporting a drug through the wall means into the formulation chamber, the electrotransport device comprising:
  (1) a reservoir comprising an intravenously administrable drug; and,
  (2) a pair of electrodes in spaced relation for providing electrical current for migrating a drug from the electrotransport drug reservoir and through the wall means into the formulation chamber.

36. A parenteral delivery system for administering a parenterally administrable drug to a patient wherein the parenteral delivery system comprises:
(a) a primary path, said primary path comprising:
  (1) a reservoir comprising a pharmaceutically acceptable fluid;
  (2) a drip chamber in fluid communication with the reservoir and comprising means for conveying fluid from the drug chamber to the patient; and,
(b) a by-pass that circumvents the primary path and comprises means for connecting thereto, said by-pass comprising:
  (3) a formulation chamber comprising:
  (4) wall means for permitting an iontophoretically delivered drug to pass therethrough;
  (5) an electrotransport device positioned on the outside of the formulation chamber, said electrotransport device comprising;
    (i) a drug reservoir comprising an ionizable drug; and,
    (ii) a pair of electrodes for providing an electrical current for iontophoretically delivering an ionized drug from the drug reservoir from the outside through the wall means for permitting an iontophoretically delivered drug to pass therethrough; and,
(c) means for delivering the drug from the formulation chamber to the means for conveying fluid to the patient.

* * * * *

UNITED STATES PATENT AND TRADEMARK OFFICE
CERTIFICATE OF CORRECTION

PATENT NO. : 4,978,337

DATED : December 18, 1990

INVENTOR(S) : Felix Theeuwes

It is certified that error appears in the above-identified patent and that said Letters Patent is hereby corrected as shown below:

Column 11, in claim 10, in line 9, delete "12" and insert ----16----;

Column 11, in claim 10, in line 10, delete "pat" and insert ----path----.

Signed and Sealed this

Twenty-fourth Day of December, 1991

*Attest:*

HARRY F. MANBECK, JR.

*Attesting Officer*   *Commissioner of Patents and Trademarks*